United States Patent [19]
Rosazza et al.

[11] Patent Number: 5,856,158
[45] Date of Patent: Jan. 5, 1999

[54] PURIFIED NITRIC OXIDE SYNTHASE FROM RAT BRAIN

[75] Inventors: John P. N. Rosazza; Yijun Chen, both of Iowa City, Iowa

[73] Assignee: University of Iowa Research Foundation, Iowa City, Iowa

[21] Appl. No.: 675,821

[22] Filed: Jul. 5, 1996

[51] Int. Cl.$^6$ .............................. C12N 9/06; C12N 5/06; A61K 35/30
[52] U.S. Cl. .......................... 435/191; 435/335; 424/570
[58] Field of Search ..................... 435/191, 184, 435/189, 335; 424/94.4, 570

[56] References Cited

U.S. PATENT DOCUMENTS

| 5,268,465 | 12/1993 | Bredt et al. | 435/525.3 |
| 5,468,630 | 11/1995 | Billiar et al. | 435/189 |
| 5,498,539 | 3/1996 | Harrison et al. | 435/365 |

OTHER PUBLICATIONS

Webster's II New Riverside University Dictionary. (1994) (The Riverside Publishing Co.: Boston) pp. 646 and 958.
Cote et al. "Nitric oxide systhase in the cat brain: cofactors–enzyme–substrate interaction", Free Radical Biology and Medicine (Apr. 8, 1996) 21(1): 109–115.
Kent "Chemical synthesis of peptides and proteins", Ann. Rev. Biochem. (1988), 57: 957–89.
Austin et al., "A study of the action of bradykinin and bradykinin analogues in the human nasal airway," *J. Physiol.* 478:351–356 (1994).
Bhoola, "Bioregulation of kinins: kallikreins, kininogens, and kininases," *Pharmacol. Rev.* 44:1–58 (1992).
Bredt and Snyder, "NItric oxide mediates glutamate–linked enhancement of cGMP levels in the cerebellum," *Proc. Natl. Acad. Sci. USA* 86:9030–9033 (1989).
Bredt and Snyder, "Isolation of nitric oxide synthase, a calmodulin–requiring enzyme," *Proc. Natl. Acad. Sci. USA* 87:682–685 (1990).
Bredt et al., "Cloned and expressed nitric oxide synthase structurally resembles cytochrome P–450 reductase," *Nature* 351:714–718 (1991).
Bredt et al., "Nitric oxide synthase regulatory sites," *J. Biol. Chem.* 267:10976–10981 (1992).
Burnett et al., "Nitric oxide: a physiologic mediator of penile erection," *Science* 257:401–403 (1992).
Busse and Mulsch, "Calcium–dependent nitric oxide synthase in endothelial cytosol is mediated by calmodulin," *FEBS Lett.* 265:133–136 (1990).
Chen and Rosazza, "A bacterial nitric oxide synthase form a Nocardia species," *Biochem. Biophys. Res. Commun.* 203:1251–1258 (1994).
Chen and Rosazza, "Purification and characterization of nitric oxide synthase ($NOS_{Noc}$) from a Nocardia species," *J. Bacteriol.* 177:5122–5128 (1995).
Corbett et al., "Interleukin–1β–induced formation of EPR–detectable iron–nitrosyl complexes in Islets of Langerhans," *J. Biol. Chem.* 266:21351–21354 (1991).

Evans et al., "Purification of a distinctive form of endotoxin–induced nitric oxide synthase from rat liver," *Proc. Natl. Acad. Sci. U. S. A.* 89:5361–5365 (1992).
Feelish et al., "Correlation between nitric oxide formation during deregulation of organic nitrates and activation of guanylate cyclase," *Eur. J. Pharmacol.* 139:19–30 (1987).
Forstermann et al., "Isoforms of nitric oxide synthase," *Biochem. Pharmacol.* 42:1849–1857 (1991).
Griffith et al., "Nitric oxide synthases," *Annu. Rev. Physiol.* 57:707–736 (1995).
Hecker et al., The metabolism of L–arginine and its significance for the biosynthesis of endothelium–derived relaxing factor: Cultured endothelial cells recycle L–citrulline to L–arginine, *Proc. Natl. Acad. Sci. USA* 87:8612–8616 (1990).
Hecker et al., "On the substrate specificity of nitric oxide synthase," *FEBS Lett.* 294:221–224 (1991).
Hecker et al., "Characteriztion of a microsomal calcium–dependent nitric oxide synthase in activated J774.2 monocyte/macrophages," *J. Cardiovasc. Pharmacol.* 20:S139–S141 (1992).
Hevel et al., "Purification of the inducible murine macrophage nitric oxide synthase," *J. Biol. Chem.* 266:22789–22791 (1991).
Hibbs et al., "Macrophage cytotoxicity: Role for L–arginine deiminase and imino nitrogen oxidation to nitrate," *Science* 235:473–476 (1987).
Hiki et al., "Purification of insoluble nitric oxide synthase from rat cerebellum," *J. Biochem.* 111:556–558 (1992).
Ignarro et al., "Endothelium–derived relaxing factor produced and released from artery and vein is nitric oxide," *Proc. Natl. Acad. Sci. USA* 85:9265–9269 (1987).
Kiechle et al., "Nitric Oxide," *Am. J. Clin. Pathol.* 100:567–575 (1993) (1990).
Klatt et al., "Multiple catalytic functions of brain nitric oxide synthase," *J. Biol. Chem.* 268:14781–14787 (1993).
Knowles et al., "Differential induction of brain, lung and liver nitric oxide synthase by endotoxin in the rat," *Biochem. J.* 270:833–836 (1990).
Knowles et al., "Nitric oxide synthases in mammals," *Biochem. J.* 298:249–258 (1994).
Kwon et al., "L–citrulline production from L–arginine by macrophage nitric oxide synthase," *J. Biol. Chem.* 265:13442–13445 (1990).

(List continued on next page.)

*Primary Examiner*—Jon P. Weber
*Assistant Examiner*—Susan Hanley
*Attorney, Agent, or Firm*—Zarley, McKee, Thomte, Voorhees & Sease

[57] ABSTRACT

A nitric oxide synthase (NOS) protein is obtained from rat brain and purified to a specific activity at least 6,360-fold that of a crude tissue preparation. The NOS protein has a denatured MW of 105 kD determined by SDS-PAGE, a dimeric MW of 230 kD determined by gel filtration and requires FAD, FMN, $Ca^{2+}$ and tetrahydropterin for the production of nitric oxide from L-arginine or an arginine-rich peptide, oligopeptide or protein substrate.

7 Claims, 2 Drawing Sheets

OTHER PUBLICATIONS

Lamas et al., "Endothelial nitric oxide synthase: molecular characterization of a distinct constitutive enzyme isoform," *Proc. Natl. Acad. Sci. U. S. A.* 89:6348–6352 (1992).

Lammek et al., "A new highly potent anatagonist of bradykinin," *Peptides* 11:1041–1043 (1990).

Lammek et al., "A novelbradykinin antagonist with improved properties," *J. Phar. Pharmacol.* 43:887–888 (1991).

Leone et al., "Constitutive and inducible nitric oxide synthases incorporate molecular oxygen into both nitric oxide and citrulline," *J. Biol. Chem.* 266:23790–23795 (1991).

Lowenstein et al., "Cloned and expressed macrophage nitric oxide synthase contrasts with the brain enzzyme," *Proc. Natl. Acad. Sci. U. S. A.* 89:6711–6715 (1992).

Lyons et al., "Molecular cloning and functional expression of an inducible nitric oxide synthase from a murine macrophage cell line," *J. Biol. Chem.* 267:6370–6374 (1992).

Marletta, "Nitric oxide synthase structure and mechanism," *J. Biol. Chem.* 268:12231–12234 (1993).

Mayer et al., "Purification of a $Ca^{2+}$/calmodulin–dependent nitric oxide synthase from porcine cerebellum," *FEBS Lett.* 277:215–219 (1990).

McMillan etal., "Cloned expressed rat cerebellar nitric oxide synthase contains stoichiometric amounts of heme, which binds carbon monoxide," *Proc. Natl. Acad. Sci. USA* 89:11141–11145 (1992).

Mulligan et al., "Lung injury after deposition of IgA immune complexes," *J. Immunol.* 148:3086–3092 (1992).

Nathan, "Nitric oxide as a secretory product of mammalian cells," *FASEB J.* 6:3051–3064 (1992).

Ohshima et al., "Purification of nitric oxide synthase from bovine brain: immunological characterization and tissue distribution," *Biochem. Biophys. Res. Commun.* 183:238–244 (1992).

Olken et al., "Inactivation of macrophage nitric oxide synthase activity by $N^G$–methyl–L–arginine," *Biochem. Biophys. Res. Commun.* 177:828–833 (1991).

Palmer et al., "Nitric oxide release amouunts for the biological activity of endothelium–derived relaxing factor," *Nature* 327:524–526 (1987).

Palmer et al., "Vascular endothelial cells synthesizenitric oxide from L–arginine," *Nature* 333:664–666 (1998).

Perrella, "EZ–FIT: A practical curve–fitting microcomputer program for the analysis of enzyme kinetic data on IBM–PC compatible computers," *Anal Biochem.* 174:437–447 (1988).

Pufahl et al., "Mechanistic probes of N–hydroxylation of L–arginine by the inducible nitric oxide synthase from murine macrophages," *Biochemistry* 31:6822–6828 (1992).

Regoli et al., "Pharmacology of bradykinin and related kinins," *Pharmacol. Rev.* 32:1–46 (1980).

Schmidt et al., "Purification of a soluble isoform of guanylyl cyclase–activating–factor synthase," *Proc. Natl. Acad. Sci. U. S. A.* 88:365–369 (1991).

Sherman et al., "Purification and cDNA sequence of an inducible nitric oxide synthase from a human tumor cell line," *Biochemistry* 32:11600–11605 (1993).

Stuehr et al., "Purification and characterization of the cytokine–induced macrophage nitric oxide synthase: an FAD–and FMN–containing flavoprotein," *Proc. Natl. Acad. Sci. U. S. A.* 88:7773–7777 (1991)

Stuehr et al., "$N^\omega$–hydroxy–L–arginine is an intermediate in the biosynthesis of nitric oxide from L–arginine," *J. Biol. Chem.* 266:6259–6263 (1991).

Stuehr et al., "Spectral characterization of brain and macrophage nitric oxide synthases," *J. Biol. Chem.* 267:20547–20550 (1992).

Wallace et al., "$N^\omega$hydroxy–L–arginine: a novel arginine analog capable of causing vasorelaxation in bovine intrapulmonary artery," *Biochem. Biophys. Res. Commun.* 176:528–534 (1991).

White et al., "Nitric oxide synthase is a cytochrome P–450 type hemoprotein," *Biochemistry* 31:6627–6631 (1992).

Wood et al., "Vascular smooth muscle–derived relaxing factor (MDRF) and its close similarity to nitric oxide," *Biochem. Biophys. Res. Comm.* 170:80–88 (1990).

Xie et al., "Cloning and characterization of inducible nitric oxide synthase from mouse macrophages," *Science* 256:225–228 (1992).

Yui et al., "Calmodulin–independent nitric oxide synthase from rat polymorphonuclear neutrophils," *J. Biol. Chem.* 266:3369–3371 (1991).

PURIFIED NITRIC OXIDE SYNTHASE FROM RAT BRAIN

BACKGROUND OF THE INVENTION

1. Field of the Invention

The present invention is directed to a purified enzyme and, more particularly, to a novel, purified, constitutive mammalian nitric oxide synthase (NOS) that utilizes both L-arginine and arginine-rich peptides, oligopeptides (e.g., bradykinin (BK)), and proteins as substrates.

2. Description of Related Art

Nitric oxide synthases (NOS, EC 1.14.23) are important enzymes, which convert L-arginine to L-citrulline and nitric oxide (NO). Nitric oxide is a very short-lived free radical, which is rapidly oxidized to nitrite ($NO_2$) and nitrate ($NO_3$) which are measured as the stable inactive end products of nitric oxide formation. The significance, however, lies in the fact that NO appears to play a pivotal role in a wide variety of physiological and pathological processes in mammals. These processes include vasodilation and regulation of normal vascular tone, inhibition of platelet aggregation, neuronal transmission, cytostasis, hypotension associated with endotoxic shock, inflammatory response-induced tissue injury, mutagenesis, and formation of carcinogenic N-nitrosamines (Nathan, *FASEB J.* 6:3051–3064 (1992); Kiechle et al., *Am. J. Clin. Pathol.* 100:567–575 (1993)). For example, it is well-known in the art to treat humans afflicted with angina distress and cardiovascular disease with nitroglycerin, which acts as a vasodilating agent. In the body, nitroglycerin is converted to nitric oxide (NO), which is the pharmacologically active metabolite. See, Palmer et al., *Nature* 333:664–666 (1988). Thus, evidence that NO mediates functions as diverse as those which occur in the brain, the endothelium and the blood, has led to intense study into the biological roles of NO and the various distinct members of the NOS family. (See, e.g., Marletta, *J. Biol. Chem.* 268:12231–12234 (1993); Knowles et al., *Biochem. J.* 298:249–258 (1994)).

It is well known by those skilled in the art that multiple isoforms of the NOS enzyme exist and that they are generally classified into two broad categories: 1) constitutive and 2) inducible. These classes of NOS enzymes vary considerably in their size, amino acid sequence, activity and regulation, and exhibit a number of substantial differences, indicating differences in their molecular structures. Increasingly diverse biological functions are being attributed to the NO formed by these three major known types of NOS (Nathan, *FASEB J.* 6:3051 (1992); Marletta, *J. Biol. Chem.* 268:12231 (1993); Knowles et al., *Biochem. J.* 298:249 (1994); Griffith et al., *Annu. Rev. Physiol.* 57:707 (1995)). For example, cells such as neurons and vascular endothelial cells contain constitutive NOS isotypes, while macrophages and vascular endothelial cells express an inducible NOS.

Several isoforms of NOS's from different mammalian tissues and cells have been purified and characterized; in brain (nNOS) by Bredt and Snyder, *Proc. Natl. Acad. Sci. USA* 87:682–685 (1990); in endothelial cells (eNOS) by Forstermann et al., *Biochem. Pharmacol.* 42:1849–1857 (1991); in macrophages (iNOS) by Hibbs et al., *Science* 235:473 (1987) and Stuehr et al., *Proc. Natl. Acad. Sci. U.S.A.* 88:7773–7777 (1991); in hepatocytes by Knowles et al., *Biochem. J.* 279:833–836 (1990); in vascular cells by Wood et al., *Biochem. Biophys. Res. Comm.* 170:80–88; in neutrophils by Yui et al., *J. Biol. Chem.* 266:12544–12547 (1991) and Yui et al., *J. Biol. Chem.* 266:3369–3371 (1991); and in other tissues (see, e.g., Hevel et al., *J. Biol. Chem.* 266:22789–22791 (1991); Mayer et al., *FEBS Lett.* 277:215–219 (1990); Schmidt et al., *Proc. Natl. Acad. Sci. U.S.A.* 88:365–369 (1991); Ohshima et al., *Biochem. Biophys. Res. Commun.* 183:238–244 (1992); Hiki et al., *J. Biochem.* 111:556–558 (1992); Evans et al., *Proc. Natl. Acad. Sci. U.S.A.* 89:5361–5365 (1992); Sherman et al., *Biochemistry* 32:11600–11605 (1993)). U.S. Pat. No. 5,268,465 claims a cDNA molecule encoding all or a portion of a mammalian calmodulin-dependent nitric oxide synthase (nNOS), comprising between 12 and 4,000 nucleotides. U.S. Pat. No. 5,468,630 claims an isolated nucleic acid molecule comprising the nucleic acid sequence encoding a human inducible nitric oxide synthase (iNOS) protein. U.S. Pat. No. 5,498,539 claims an isolated nucleic acid molecule comprising the nucleic acid sequence encoding a bovine endothelial nitric oxide synthase (eNOS) protein having amino acid or nucleic acid sequences set forth in the specification.

It is also known that small amounts of NO generated by a constitutive NOS appear to act as a messenger molecule by activating soluble guanylate cyclase and, thus, increasing intracellular guanosine, 3', 5'-cyclic monophosphate (cGMP) and the induction of biological responses that are dependent on cGMP as a secondary messenger. For example, through this mechanism, endothelial derived NO induces relaxation of vascular smooth muscle and is identified as endothelium derived relaxing factor (Palmer et al., *Nature* 327:524–526 (1987) and Ignarro et al., *Proc. Natl. Acad. Sci. USA* 84:9265–9269 (1987)). In addition, neuronal nitric oxide can act as a neuro-transmitter by activating guanylate cyclase with important functions in the central nervous system and autonomic nervous systems. Bredt and Snyder, *Proc. Natl. Acad. Sci. USA* 86:9030–9033 (1989) and Burnett et al., *Science* 257:401–403 (1992). Moreover, various purified NOS enzymes have been identified as hemeproteins (Stuehr et al., *J. Biol. Chem.* 267:20547–20550 (1992); White et al., *Biochemistry* 31:6627–6631 (1992); McMillan et al., *Proc. Natl. Acad. Sci. USA* 89:11141–11145 (1992)) and flavoproteins (Hevel et al., *J. Biol. Chem.* 266:22789–22791 (1991); Bredt et al., *J. Biol. Chem.* 267:10976–10981 (1992)).

Thus, the catalytic mechanisms of the NOS enzymes have also been the subject of great interest (see, e.g., Marletta, *J. Biol. Chem.* 268:12231–12234 (1993)). Stable isotope studies have shown when that when L-arginine is the substrate for the enzyme, NO derives from one of the two equivalent guanidino nitrogens on the arginine moiety (Ignarro et al., 1987; Palmer et al., 1988), and that di-oxygen is the source of the oxygen atoms incorporated into citrulline and NO (Kwon et al., *J. Biol. Chem.* 265:13442–13445 (1990); Leone et al., *J. Biol. Chem.* 266:23790–23795 (1991)). Moreover, $N^G$-hydroxy-L-arginine has been demonstrated to be an oxidative intermediate in the catalytic process (Stuehr et al., *J. Biol. Chem.* 266:6259–6263 (1991); Wallace et al., *Biochem. Biophys. Res. Commun.* 176:528–534 (1991); Pufahl et al., *Biochemistry* 31:6822–6828 (1992); Klatt et al., *J. Biol. Chem.* 268:14781–14787 (1993)).

Co-factors involved in the conversion of L-arginine to L-citrulline and NO synthesis include tetrahydrobiopterin ($BH_4$), flavin adenine nucleotide (FAD), the flavin-ribitol phosphate part of FAD (FMN) and the reduced form of nicotinamide adenine dinucleotide phosphate (NADPH). In addition, when the NOS enzyme has been derived from brain or endothelial cells, calcium and calmodulin are also required. (Bredt et al., *Nature* 351:714–718 (1991); Lamas et al., *Proc. Natl. Acad. Sci. U.S.A.* 89:6348–6352 (1992); Lyons et al., *J. Biol. Chem.* 267:6370–6374 (1992); Lowenstein et al., *Proc. Natl. Acad. Sci. U.S.A.* 89:6711–6715

(1992); Xie et al., *Science* 256:225–228 (1992)). Calmodulin is a well-known protein binder for $Ca^{2+}$, ubiquitously found in plant and animal cells. The $Ca^{2+}$-calmodulin complex thus formed is known to bind to various target proteins in the cell, and thereby alter their activity.

Thus, it will be appreciated that nitric oxide has both normal physiologic intracellular and extracellular regulatory functions. However, excessive production of nitric oxide is detrimental. For example, when vascular endothelial cells are stimulated to express a NOS enzyme by a bacterial endotoxin, such as for example bacterial lipopolysaccharide (LPS), and inflammatory cytokines are elevated, the excess amounts of nitric oxides that are produced contribute to the vascular collapse seen in sepsis. Busse and Mulsch, *FEBS Lett.* 265:133–136 (1990). It is also known that when vascular cells are stimulated to express a NOS enzyme by inflammatory cytokines, the excess amounts of nitric oxides cause massive dilation of blood vessels and sustained hypotension commonly encountered in septic shock, and contribute to the eventual vascular collapse seen in sepsis. Id. It is also known that overproduction of nitric oxide in the lungs stimulated by immune complexes directly damages the lung. Mulligan et al., *J. Immunol.* 148:3086–3092 (1992). Induction of nitric oxide synthase in pancreatic islets impairs insulin secretion and contributes to the onset of juvenile diabetes. Corbett et al., *J. Biol. Chem.* 266:21351 (1991).

Thus, it will be appreciated that there is a great need in the medical community for the ability to control and regulate specific forms of NOS, particularly given its role in maintaining normal blood pressure and the devastating effect of excess NO on the cardiovascular, gastrointestinal and respiratory systems in humans. Thus considerable research has been expended to discover inhibitors and regulators of NOS activity. However, until the present invention, researchers have limited their work almost exclusively to the premise that L-arginine is the most physiologically relevant substrate of NOS. The studies have extended no further than the fact that dipeptides, such as Arg-Arg and Arg-Phe are also oxidized by crude NOS preparations derived from cultured endothelial cells and macrophages (Hecker et al., *FEBS Lett.* 294:221 (1991); Hecker et al., *Proc. Natl. Acad. Sci. USA* 87:8612 (1990); Hecker et al., *J. Cardiovasc. Pharmacol.* 20:S139 (1992)). Thus, although there have been many publications directed to analyses of arginine analogs or derivatives which inhibit NOS activity by blocking the use of arginine as a substrate for NO synthesis, or to the cofactors necessary for the conversion of arginine, no one until the present inventors has considered peptide, oligopeptide or protein substrates for the NOS enzyme. Hence, given the expectation that natural or synthetic arginine-rich peptide, oligopeptide or protein antagonists can function as NOS inhibitors, the present invention will greatly expand the number and types of inhibitors available for the regulation and control of NO production in the body. In addition, the use of a NOS to supply deficient individuals with NO-forming capability will be greatly enhanced by the purification of the nNOS-II class of enzymes. The present invention, therefore, will also provide many new ways to study the biological mechanisms involved in NO synthesis.

SUMMARY OF THE INVENTION

The present invention relates to a novel constitutive nitric oxide synthase, referred to hereinafter as nNOS-II, that has been purified from mammalian neural tissue, and which is capable of utilizing arginine-rich peptides, polypeptides and proteins (e.g., bradykinin), as well as L-arginine, as substrates. Unlike previously defined NOS isoforms, nNOS-II is unique in that it is calmodulin-dependent with L-arginine as substrate, but calmodulin-independent with an arginine-rich polypeptide, such as bradykinin (BK), as substrate. When BK is the substrate, both the N- and the C-terminal arginines of the oligopeptide are oxidized to citrullines by nNOS-II. See Equation I.

-continued (I)

Moreover, with BK as substrate, NOS activity is competitively inhibited by $N^G$-methyl-, $N^G$-nitro-L-arginines, and BK receptor-antagonists, including oligopeptide BK receptor-antagonists.

More particularly, the present invention relates to a substantially purified nNOS-II protein.

In another embodiment, the present invention relates to a mammalian brain-derived nitric oxide synthase protein purified to an activity at least 6,360-fold, said protein having a denatured molecular mass as determined by sodium dodecyl sulfate polyacrylamide gel electrophoresis under reducing conditions of about 105 kD, and a native homodimeric molecular mass as determined by gel filtration of about 230 kD, requiring NADPH, FAD, FMN, $Ca^{2+}$ and tetrahydrobiopterin cofactors for the production of nitric oxide either from L-arginine, or an analog or derivative thereof, or from an arginine-rich peptide, oligopeptide, or protein substrate. As used herein, the term "peptide" is arbitrarily defined as a peptide chain having a single peptide bond, "oligopeptide" is a peptide chain having from 2 to 14 peptide bonds, inclusive, and "protein" is a peptide chain having 15 or more peptide bonds. "Polypeptide" is intended to be generic to "oligopeptide" and "protein." "Arginine-rich" means that the peptide, oligopeptide, or protein has at least one sterically accessible arginine moiety.

In another embodiment, the present invention relates to a method of regulating or controlling nitric oxide production in a mammalian subject comprising administering to the mammal a nitric oxide-regulating amount of a peptide, oligopeptide, or protein inhibitor of nitric oxide synthase, preferably nNOS-II. As used herein, "mammalian subject" is intended to include human subjects.

In one embodiment, the present invention relates to a method of reducing the rate of nitric oxide production in a mammalian subject comprising administering to the mammal a nitric oxide inhibiting amount of a peptide, oligopeptide or protein inhibitor of nitric oxide synthase, preferably nNOS-II. "Reducing the rate" is intended to include a reduction to zero, in which case the reduction would be understood to include, not only a decrease in the rate of NO production or of the quantity of NO produced, but also a prevention of excess NO production.

In another embodiment, the present invention relates to a method of enhancing the rate of nitric oxide production in a mammalian subject comprising administering to the mammal a nitric oxide enhancing amount of nitric oxide synthase, preferably nNOS-II. "Enhancing the rate" is intended to include a stimulating, inducing or causing production of NO in a NO-deficient or NO-defective subject, in which case the enhancement would be understood to include stimulation, induction or initialization of NO production in such subjects or individuals, as well as increasing the rate of NO production or the quantity of NO produced.

In still another embodiment, the present invention relates to a method of preventing or treating a nitric oxide-mediated disease or condition in a mammalian subject comprising administering to the subject in need of such prevention or treatment a therapeutically effective amount of a peptide, oligopeptide, or protein inhibitor of nitric oxide synthase, preferably nNOS-II.

Additional objects, advantages and novel features of the invention will be set forth in part in the description which follows, and in part will become apparent to those skilled in the art on examination of the following, or may be learned by practice of the invention.

BRIEF DESCRIPTION OF THE DRAWINGS

FIG. 3 depicts HPLC chromatograms of nNOS-II reactions with BK or $Cit^1$-BK. Sensitivities of the regions at 20–30 minutes are expanded 3-fold.

DESCRIPTION OF THE PREFERRED EMBODIMENTS

The present invention is directed to a novel constitutive mammalian nitric oxide synthase (NOS) that utilizes arginine-rich peptides, oligopeptides (e.g., bradykinin), and proteins, as well as L-arginine, as substrates. The present invention was begun following an earlier discovery by the inventors of a novel bacterial NOS that utilized a range of arginine-containing polypeptides, including BK and related BK analogs ranging from 6-mer to 11-mer, to produce nitric oxide. (See, Chen and Rosazza, *Biochem. Biophys. Res. Commun.* 203:1251 (1994) and Chen and Rosazza, *J. Bacteriol.* 177:5122 (1995)).

Although increasingly diverse biological functions are being attributed to NO formed by three major known types of NOS (Nathan, *FASEB J.* 6:3051–3064 (1992); Marletta, *J. Biol. Chem.* 268:12231–12234 (1993); Knowles et al., *Biochem. J.* 298:249–258 (1994); Griffith et al., *Annu. Rev. Physiol.* 57:707–736 (1995)), there are no known published reports of arginine-containing oligopeptides, polypeptides or proteins acting as a substrate for any NOS enzyme. To the contrary, throughout the prior art, L-arginine is currently recognized as the only physiologically relevant NOS-substrate.

The present inventors found that upon purification of crude supernatant preparations from rat cerebellum using weak anion exchange chromatography (DEAE-agarose), the elution profile reproducibly produces two calmodulin-dependent neuronal nitric oxide synthase (nNOS) peaks with L-arginine as substrate. Both peaks display the characteristic calmodulin-dependent nNOS activity using L-arginine as substrate, as described by Bredt et al., *PNAS* 87:682(1990). However, the novel enzyme of the second peak (fractions 15–21), which has not been studied in the prior art, further displays unique calmodulin-independent nNOS activity in the presence of an arginine-rich polypeptide substrate, such as BK. (NOS is measured by the conversion of oxyhemoglobin to methemoglobin.) This novel nitric oxide synthase has been purified to afford a 6,360-fold purified enzyme preparation, and designated nNOS-II. When a species of nNOS-II acts upon a particular substrate, such as BK, the enzyme name may further denominate the substrate, e.g., $nNOS_{BK}$. It should be emphasized, however, that BK is only one of many peptide, oligopeptide or protein substrates for nNOS-II.

Purified nNOS-II has a $M_r$ of 105 kD by SDS-PAGE analysis and an apparent native $M_r$ of 230 kD by gel filtration, indicating that the enzyme is a homodimeric protein. By comparison, the previously described, purified nNOS enzyme migrates as a single 160 kD band on SDS-PAGE, and the native enzyme appears to be a monomer. However, both enzymes require the presence of NAPDH, FAD, FMN, $Ca^{2+}$, and tetrahydrobiopterin cofactors for substrate oxidation to occur.

When calmodulin is present with the necessary cofactors, nNOS-II also oxidizes L-arginine, but at a $K_M$ of 10.6 $\mu$M, slightly higher than the previously reported $K_M$ of 2 $\mu$M for nNOS. ($K_M$ is the substrate concentration that allows the reaction to proceed at one-half its maximum rate.) Moreover, with an L-arginine substrate, the rate of reaction, $V_{max}$, value displayed by nNOS-II is 0.85 $\mu$mol/min/mg protein, while that reported for the nNOS of the prior art is 0.96 $\mu$mol/min/mg protein. ($V_{max}$ refers to the rate of the enzyme-reaction, depending only upon how rapidly the substrate molecule can be processed. This rate when divided by the enzyme concentration provides the turnover number.)

Finally, numerous reports describe the abolishment of nNOS activity (as defined by Bredt and Snyder) by the addition of quantities of L-arginine analog inhibitors. However, in marked contrast, with nNOS-II, using BK as substrate, $N^G$-methyl-L-arginine(L-NMA) and $N^G$-nitro-L-arginine(L-NNA) were found to be reversible competitive inhibitors with apparent Ki values of 8.6 $\mu$M and 23.8 $\mu$M, respectively. These values are significantly different for the reported Ki values for L-NMA of 1.4 $\mu$M and for L-NNA of 4.4 $\mu$M for nNOS with L-arginine as substrate.

Thus, the present invention comprises a novel isoform of nitric oxide synthase, herein designated as nNOS-II, which can be readily distinguished from all previously reported NOS species, including nNOS. The broader implications of this discovery include the future identification of a new class of native, recombinant, or synthetic peptides that will function as NOS inhibitors for the modulation of cardiovascular, gastrointestinal, or bronchial activities, for contraceptive control, for the management of opioid withdrawal or cocaine-induced toxicity, or for the prevention or treatment of certain nitric oxide-mediated pathogenic conditions, such as ischemic stroke, diabetes, systemic hypotension, multiple sclerosis, Huntington's disease, Parkinson's disease, Alzheimer's disease, and the like.

It will be understood by those skilled in the art that the present invention is not limited to the use of any specific peptide, oligopeptide or protein as the substrate for the nNOS-II, although preferred substrates will be arginine-rich peptides, oligopeptides or proteins. More preferrably, the tertiary structure of such a peptide, oligopeptide or protein substrate will be such that one or more arginine groups are available to the NOS enzyme. It is most preferred that the substrate be an oligopeptide of managable size, such as from 6 to 11 amino acid residues, wherein both the α and ω amino acids are arginine.

Exemplary peptides, oligopeptides and proteins upon which nNOS-II have been shown to be active are set forth in Table 1:

TABLE 1

Arginine-Containing Peptides or Oligopeptides as Substrates for nNOS-II[a]

| Peptide | Amino Acid Sequence | Relative Activity (%) |
| --- | --- | --- |
| L-arginine | N/A[b] | 100[c] |
| Poly-arginine ($M_r$ 5,000) | N/A | 30 |
| BK | Arg—Pro—Pro—Gly—Phe—Ser—Pro—Phe—Arg (SEQ ID NO:1) | 125 |
| Des—Arg[1]—BK | Pro—Pro—Gly—Phe—Ser—Pro—Phe—Arg (SEQ ID NO:2) | 94 |
| Des—Arg[9]—BK | Arg—Pro—Pro—Gly—Phe—Ser—Pro—Phe (SEQ ID NO:3) | 180 |
| BK fragment 1–7 | Arg—Pro—Pro—Gly—Phe—Ser—Pro (SEQ ID NO:4) | 80 |
| BK fragment 1–5 | Arg—Pro—Pro—Gly—Phe (SEQ ID NO:5) | 61 |

TABLE 1-continued

Arginine-Containing Peptides or Oligopeptides as Substrates for nNOS-II[a]

| Peptide | Amino Acid Sequence | Relative Activity (%) |
| --- | --- | --- |
| BK fragment 2–7 | Pro—Pro—Gly—Phe—Ser—Pro (SEQ ID NO:6) | 0 |
| [Lys[1]]—BK | Lys—Pro—Pro—Gly—Phe—Ser—Pro—Phe—Arg (SEQ ID NO:7) | 113 |
| Lys—BK | Lys—Arg—Pro—Pro—Gly—Phe—Ser—Pro—Phe—Arg (SEQ ID NO:8) | 116 |
| Ile—Ser—BK | Ile—Ser—Arg—Pro—Pro—Gly—Phe—Ser—Pro—Phe—Arg (SEQ ID NO:9) | 110 |
| Met—Lys—BK | Met—Lys—Arg—Pro—Pro—Gly—Phe—Ser—Pro—Phe—Arg (SEQ ID NO:10) | 0 |

[a]Standard enzymatic assay was carried out to measure initial velocity of the enzymatic reaction. Purified nNOS-II 0.2 µg (specific activity for BK, 280 nmole NO formed/min/mg protein) was used for the assays. Substrate concentrations were 100 µM except for poly-arginine used with 5 µg/ml.
[b]Not applicable.
[c]Activity for arginine is expressed as 100%. The values are the means of three measurements.

This list, however, is intended to be merely exemplary, not limiting in scope.

A model substrate of nNOS-II is the nonapeptide bradykinin (Arg-Pro-Pro-Gly-Phe-Ser-Pro-Phe-Arg) (SEQ ID NO:1). BK was selected as a convenient and available model oligopeptide substrate for displaying the catalytic properties of nNOS-II because:

it contains positionally different N- and C-terminal arginine residues;

its recognized physiological role in both cardiovascular and central nervous systems has been well characterized;

it displays physiological and pharmacological effects similar to those ascribed to NO; and it has been linked as an apparent mediator of NOS activity (Regoli et al., *Pharmacol. Rev.* 32:1–46 (1980); Bhoola, *Pharmacol. Rev.* 44:1–58 (1992)).

In addition, BK is of ideal size (containing 9 amino acid residues) for conversion by the nNOS-II enzyme.

In a preferred embodiment, the present invention provides substantially pure nNOS-II protein. One specific enzyme herein provided in purified form is nNOS-II. When used with regard to nNOS-II of the present invention, the terms "protein" and "enzyme" are used interchangeably, even though technically an enzyme is a specific subset of the category "protein." Moreover, as used herein, a protein is said to be "highly purified" or "substantially pure" if the specific activity of the protein cannot be significantly incresed by further purification, and if the specific activity is greater than that found in whole cell extracts containing the protein.

Any eukaryotic organism can be used as a source of nNOS-II, or the genes encoding same, as long as the source organism naturally contains the enzyme or its equivalent. As used herein, "source organism" refers to the original organism from which the amino acid or DNA sequence is derived, regardless of the organism the enzyme expressed in or ultimately isolated from. For example, a human is said to be the "source organism" of nNOS-II expressed by a bacterial expression system as long as the amino acid sequence is that of human nNOS-II. The most preferred source organism is mammalian.

A variety of methodologies known in the art can be utilized to obtain the nNOS-II proteins of the present invention. In one embodiment, the enzyme is purified from tissues or cells which naturally produce it, such as rat cerebellum. One skilled in the art can readily follow known methods for isolating proteins in order to obtain the nNOS-II proteins. These include, but are not limited to, immunochromotography, size-exclusion chromatography, ion-exchange chromatography, affinity chromatography, HPLC, and the methods set forth by example in the present disclosure. One skilled in the art can readily adapt known purification schemes to delete certain steps or to incorporate additional purification procedures.

In a preferred embodiment of the invention, nNOS-II may be purified using column chromatography. Specifically, it has been found that greater than one-thousand-fold purification can be achieved using an affinity chromatography column. Since NADPH is a necessary cofactor for enzyme activity, if one employs a solid matrix containing an NADPH moiety or an NADPH analog, such as dextran blue, or 2',5'-ADP agarose or 2',5'-ADP sepharose, then the NOS of the present invention will bind to the matrix. It can be eluted using a soluble form of NADPH or an analog thereof at a concentration of about 1 to about 10 mM. It is desirable that the preparation which is applied to the affinity chromatography column first be partially purified on an ion exchange column, such as, diethylaminoethyl (DEAE) agarose. Other ion exchange columns known in the art can also be used. The NOS of the present invention binds to DEAE-agarose and can be eluted with a sodium chloride gradient. The greatest peak of nNOS-II activity elutes with between about 150 mM and about 210 mM sodium chloride. A combination of these three column chromatography processes on a cleared brain homogenate will result in a homogeneous preparation, as can be demonstrated by silver staining of an SDS/PAGE-separated sample, or by Western blotting.

In another embodiment, the enzyme may be purified from cells which have been altered to express the desired protein. As used herein, a cell is said to be "altered to express a desired protein" when the cell, through genetic manipulation, is made to produce a protein which it normally does not produce, or which the cell normally produces at low levels. One skilled in the art can readily adapt procedures for introducing and expressing either genomic or cDNA sequences into either eukaryotic or prokaryotic cells, in order to generate a cell which produces the desired nNOS-II protein.

The present invention further encompasses the expression of the nNOS-II proteins (or a functional derivative thereof) in either prokaryotic or eukaryotic cells. A "functional derivative" of a sequence, either protein or nucleic acid, is a molecule that possesses a biological activity (either functional or structural) that is substantially similar to a biological activity of the protein or nucleic acid sequence. A functional derivative of a protein may or may not contain post-translational modifications such as covalently linked carbohydrate, depending on the necessity of such modifications for the performance of a specific function. The term "functional derivative" is intended to include the "fragments," "segments," "variants," "analogs," or "chemical derivatives" of a molecule.

As used herein, a molecule is said to be a "chemical derivative" of another molecule when it contains additional chemical moieties not normally a part of the molecule. Such moieties may improve the molecule's solubility, absorption, biological half life, and the like. The moieties may alternatively decrease the toxicity of the molecule, eliminate or attenuate any undesirable side effect of the molecule, and the like. Moieties capable of mediating such effects are disclosed in *Remington's Pharmaceutical Sciences* (1980). Procedures for coupling such moieties to a molecule are well known in the art.

A "variant" or "allelic or species variant" of a protein or nucleic acid is meant to refer to a molecule substantially similar in structure and biological activity to either the protein or nucleic acid. Thus, provided that two molecules possess a common activity and may substitute for each other, they are considered variants as that term is used herein even if the composition or secondary, tertiary, or quaternary structure of one of the molecules is not identical to that found in the other, or if the amino acid or nucleotide sequence is not identical.

Preferred prokaryotic hosts include bacteria such as *E. coli,* Bacillus, Streptomyces, Pseudomonas, Salmonella, Serratia, etc. Under such conditions, the nNOS-II will not be glycosylated. The prokaryotic host must be compatible with the replicon and control sequences in the expression plasmid.

However, prokaryotic systems may not prove efficacious for the expression of all proteins. While prokaryotic expression systems, e.g., pET3c, have been used to express high molecular weight proteins, such as a biologically active (molecular weight $(M_r)$~118 kDa) FGF-1:β-galactosidase chimera (Shi et al., submitted to *J. Biol. Chem.,* 1996), successful folding and disulfide bond formation may be difficult to accomplish in bacteria.

Nevertheless, to express nNOS-II (or a functional derivative thereof) in a prokaryotic cell, it is necessary to operably link the nNOS-II coding sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, etc. Examples of inducible prokaryotic promoters include the major right and left promoters of bacteriophage λ ($P_L$ and $P_R$), the trp, recA, lacZ, lacI, and gal promoters of *E. coli,* the α-amylase (Ulmanen et al., *J. Bacteriol.* 162:176–182 (1985)) and the ζ-28-specific promoters of *B. subtilis* (Gilman et al., *Gene sequence* 32:11–20 (1984)), the promoters of the bacteriophages of Bacillus (Gryczan, In: *The Molecular Biology of the Bacilli,* Academic Press, Inc., NY (1982)), and Streptomyces promoters (Ward et al., *Mol. Gen. Genet.* 203:468–478 (1986)). See also reviews by Glick (*J. Ind. Microbiol.* 1:277–282 (1987)); Cenatiempo (*Biochimie* 68:505–516 (1986)); and Gottesman (*Ann. Rev. Genet.* 18:415–442 (1984)).

Proper expression in a prokaryotic cell also requires the presence of a ribosome binding site upstream of the gene sequence-encoding sequence. Such ribosome binding sites are disclosed, for example, by Gold et al. (*Ann. Rev. Microbiol.* 35:365–404 (1981)).

Preferred eukaryotic hosts include yeast, fungi, insect cells, mammalian cells, either in vivo or in tissue culture. Mammalian cells which may be useful as hosts include HeLa cells, cells of fibroblast origin such as VERO or CHO-K1, or cells of lymphoid origin, such as the hybridoma SP2/O-AG14 or the myeloma P3×63Sg8, and their derivatives. Preferred mammalian host cells include SP2/O and J558L, as well as neuroblastoma cell lines such as IMR 332 that may provide better capacities for correct post-translational processing.

For a mammalian host, several possible vector systems are available for the expression of nNOS-II. A wide variety of transcriptional and translational regulatory sequences may be employed, depending upon the nature of the host. The transcriptional and translational regulatory signals may be derived from viral sources, such as adenovirus, bovine papilloma virus, Simian virus, or the like, where the regulatory signals are associated with a particular gene sequence which has a high level of expression. Alternatively, promoters from mammalian expression products, such as actin, collagen, myosin, etc., may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

Yeast expression systems can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., pre-peptides). Any of a series of yeast gene sequence expression systems incorporating promoter and termination elements from the actively expressed gene sequences coding for glycolytic enzymes produced in large quantities when yeast are grown in mediums rich in glucose can be utilized. Known glycolytic gene sequences can also provide very efficient transcriptional control signals. For example, the promoter and terminator signals of the phosphoglycerate kinase gene sequence can be utilized.

The more preferred host for a protein the size of nNOS-II is insect cells, for example the Drosophila larvae. Using insect cells as hosts, the Drosophila alcohol dehydrogenase promoter can be used (see, e.g., Rubin, G. M., *Science* 240:1453–1459 (1988)).

The baculovirus insect cell expression system is the most preferred system for expressing the soluble nNOS-II construct as a carboxy-terminal triple tandem myc-epitope repeat:glutathione-S-transferase (GST) fusion protein chimera, using conventional PCR methods (Zhan et al., *J. Biol. Chem.* 269:20221–20224 (1994)). These include the use of recombinant circle PCR to synthesize the soluble nNOS-II construct, the preparation and expression of the recombinant virus, AcNPV-GsJ in Sf9 cells (Summers and Smith (1988) *A Manual of Methods for Baculovirus Vectors and Insect Culture Procedures* (Texas Experimental Station Bulletin #1555)), the use of GST affinity chromatography (Zhan et al., 1994) and reversed phase or ion exchange HPLC to purify the recombinant protein from Sf9 cell lysates and Myc immunoblot analysis to monitor the purification and assess the purity of the nNOS-II protein.

The soluble nNOS-II construct may not only prove to be valuable for the baculovirus expression system, but also as a construct for the expression of a secreted and soluble nNOS-II enzyme in mammalian cells for implantation in vivo. Moreover, baculovirus vectors can be engineered to express large amounts of nNOS-II in insect cells (Jasny,

*Science* 238:1653 (1987); Miller et al., in *Genetic Engineering* (1986), Setlow et al., eds., *Plenum*, Vol. 8, pp. 277–297).

As discussed above, expression of nNOS-II in eukaryotic hosts requires the use of eukaryotic regulatory regions. Such regions will, in general, include a promoter region sufficient to direct the initiation of RNA synthesis. Preferred eukaryotic promoters include: the promoter of the mouse metallothionein I gene sequence (Hamer et al., *J. Mol. Appl. Gen.* 1:273–288 (1982)); the TK promoter of Herpes virus (McKnight, *Cell* 31:355–365 (1982)); the SV40 early promoter (Benoist et al., *Nature* (London) 290:304–310 (1981)); the yeast gal4 gene sequence promoter (Johnston et al., *Proc. Natl. Acad. Sci.* (USA) 79:6971–6975 (1982); Silver et al., *Proc. Natl. Acad. Sci.* (USA) 81:5951–5955 (1984)).

As is widely known, translation of eukaryotic mRNA is initiated at the codon which encodes the first methionine. For this reason, it is preferable to ensure that the linkage between a eukaryotic promoter and a DNA sequence which encodes nNOS-II (or a functional derivative thereof) does not contain any intervening codons which are capable of encoding a methionine (i.e., AUG). The presence of such codons results either in a formation of a fusion protein (if the AUG codon is in the same reading frame as the nNOS-II coding sequence) or a frame-shift a frame-shift mutation (if the AUG codon is not in the same reading frame as the nNOS-II coding sequence).

The nNOS-II coding sequence and an operably linked promoter may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the nNOS-II may occur through the transient expression of the introduced sequence. Alternatively, permanent expression may occur through the integration of the introduced sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, H., *Molec. Cell. Biol.* 3:280 (1983).

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids, such as those capable of replication in *E. coli* (such as, for example, pBR322, ColE1, pSC101, pACYC 184, πVX). Such plasmids are, for example, disclosed by Maniatis et al. (In: *Molecular Cloning, A Laboratory Manual*, Cold Spring Harbor Press, Cold Spring Harbor, N.Y. (1982)). Bacillus plasmids include pC194, pC221, pT127, etc. Such plasmids are disclosed by Gryczan (In: *The Molecular Biology of the Bacilli*, Academic Press, NY (1982), pp. 307–329). Suitable Streptomyces plasmids include pIJ101 (Kendall et al., *J. Bacteriol.* 169:4177–4183 (1987)), and streptomyces bacteriophages such as φC31 (Chater et al., In: *Sixth International Symposium on Actinomycetales Biology*, Akademiai Kaido, Budapest, Hungary (1986), pp. 45–54). Pseudomonas plasmids are reviewed by John et al. (*Rev. Infect. Dis.* 8:693–704 (1986)), and Izaki (*Jpn. J. Bacteriol.* 33:729–742 (1978)).

Preferred eukaryotic plasmids include BPV, vaccinia, SV40, 2-micron circle, etc., or their derivatives. Such plasmids are well known in the art (Botstein et al., *Miami Wntr. Symp.* 19:265–274 (1982); Broach In: *The Molecular Biology of the Yeast Saccharomyces:* Life Cycle and Inheritance, Cold Spring Harbor Laboratory, Cold Spring Harbor, N.Y., p. 445–470 (1981); Broach, *Cell* 28:203–204 (1982); Bollon et al., *J. Clin. Hematol. Oncol.* 10:39–48 (1980); Maniatis, In: *Cell Biology: A Comprehensive Treatise*, Vol. 3, Gene sequence Expression, Academic Press, NY, pp. 563–608 (1980)).

Once the vector or DNA sequence containing the construct(s) has been prepared for expression, the DNA construct(s) may be introduced into an appropriate host cell by any of a variety of suitable means: transformation, transfection, conjugation, protoplast fusion, electroporation, calcium phosphate-precipitation, direct microinjection, etc. After the introduction of the vector, recipient cells are grown in a selective medium, which selects for the growth of vector-containing cells. Expression of the cloned gene sequence(s) results in the production of nNOS-II, or fragments thereof. This can take place in the transformed cells as such, or following the induction of these cells to differentiate (for example, by administration of bromodeoxyuracil to neuroblastoma cells or the like).

The nNOS-II proteins (or a functional derivatives thereof) of the present invention can be used in a variety of procedures and methods, such as for the generation of antibodies, for use in identifying pharmaceutical compositions, for studying DNA/protein interaction, and for examinining the mechanism of NO synthesis.

The substantially pure peptides of the present invention may also be administered to a mammal intravenously, intramuscularly, subcutaneously, enterally, topically or parenterally. A "substantially pure" or "highly purified" protein, as defined previously, is a protein preparation that is generally lacking in other cellular components with which it is normally associated in vivo.

When administering peptides by injection, the administration may be by continuous injections, or by single or multiple injections. The peptides are intended to be provided to a recipient mammal in a "pharmacologically or pharmaceutically acceptable form" in an amount sufficient to "therapeutically effective." A peptide is considered to be in "pharmaceutically or pharmacologically acceptable form" if its administration can be tolerated by a recipient patient. An amount is said to be "therapeutically effective" (an "effective amount") if the dosage, route of administration, etc., of the agent are sufficient to effect a response to nNOS-II. Thus, the present peptides may be used to induce, increase, enhance, control, regulate or modulate the effect of the nNOS-II protein, or the synthesis and expression of NO.

In another embodiment of the present invention, methods for inhibiting, decreasing or preventing the activity of the nNOS-II protein can be achieved by providing an agent capable of binding to or inhibiting the enzyme (or a functional derivative thereof). Such agents include, but are not limited to: nNOS-II inhibitors and antagonists, antisense nNOS-II, the antibodies to nNOS-II (anti-nNOS-II), and the secondary or anti-peptide peptides of the present invention. By decreasing the activity of nNOS-II, the effect which expression of the peptide has on NO synthesis can be modified, regulated, controlled, inhibited or prevented.

In one example of the present invention, methods are presented for decreasing the activity of nNOS-II (or a functional derivative thereof) by means of an anti-sense strand of cDNA to disrupt the translation of the nNOS-II message. Specifically, a cell is modified using routine procedures such that it expresses an antisense message, a message which is complementary to the pseudogene message. By constitutively or inducibly expressing the antisense RNA, the translation of the nNOS-II mRNA can be regulated. Such antisense technology has been successfully applied to regulate the expression of poly(ADP-ribose) polymerase (see, Ding et al., *J. Biol. Chem.* 267 (1992)).

In the alternative, nNOS-II activity can be prevented or inhibited by binding the peptide, oligopeptide or protein substrate used by the enzyme, thus modifying the amount of NO can be synthesized by the enzyme. Examples of such nNOS inhibitors include peptides or petidomimetics of structures such as bradykinin B2 receptor antagonists that have demonstrated nNOS-II inhibition activity, or arginine derivatives, such as L-NNA or L-NMA. Not all bradykinin B2 receptor antagonists have nNOS-II inhibitory activity as demonstrated in the present invention; however, it is within the ordinary skill of one in the art using known techniques and the procedures herein disclosed to determine which peptides, oligopeptides or proteins are capable of nNOS-II inhibition.

On the other hand, methods for stimulating, increasing or enhancing the activity of the nNOS-II peptide can be achieved by providing an agent capable of modulating the synthesis of NO by nNOS-II (or a functional derivative thereof), or by inhibiting or preventing an inhibitory signal which would diminish or stop the activity of nNOS-II in the system. Such agents include, but are not limited to, the anti-antisense nNOS-II peptides. By enhancing the activity of nNOS-II, the effect which the enzyme has on NO synthesis can also be modified.

In yet another embodiment, nNOS-II (or a functional derivative or variant thereof) can be used to produce antibodies or hybridomas. One skilled in the art will recognize that if an antibody is desired that will bind to nNOS-II, such an antibody would be generated as described above and used as an immunogen. The resulting antibodies are screened for the ability to bind nNOS-II.

The antibodies utilized in the above methods can be monoclonal or polyclonal antibodies, as well fragments of these antibodies and humanized forms. Humanized forms of the antibodies of the present invention may be generated using one of the procedures known in the art such as chimerization or CDR grafting.

In general, techniques for preparing monoclonal antibodies are well known in the art (Campbell, *"Monoclonal Antibody Technology: Laboratory Techniques in Biochemistry and Molecular Biology,"* Elsevier Science Publishers, Amsterdam, The Netherlands (1984); St. Groth et al., *J. Immunol. Methods* 35:1–21 (1980)). For example, in one embodiment an antibody capable of binding nNOS-II is generated by immunizing an animal with a synthetic polypeptide whose sequence is obtained from a region of the nNOS-II protein.

Any animal (mouse, rabbit, etc.) which is known to produce antibodies can be utilized to produce antibodies with the desired specificity, although because of the large size of the nNOS-II molecule, the rabbit may be preferred. Methods for immunization are well known in the art. Such methods include subcutaneous or interperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/O-Ag14 myeloma cells, and allowed to become monoclonal antibody producing hybridoma cells. A hybridoma is an immortalized cell line which is capable of secreting a specific monoclonal antibody.

Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Res.* 175:109–124 (1988)).

Hybridomas secreting the desired antibodies are cloned and the class and subclass are determined using procedures known in the art (Campbell, *Monoclonal Antibody Technology: Laboratory Techniques in Biochemistry and Molecular Biology,* Elsevier Science Publishers, Amsterdam, The Netherlands (1984)).

For polyclonal antibodies, antibody containing antisera is isolated from the immunized animal and is screened for the presence of antibodies with the desired specificity using one of the above-described procedures.

Conditions for incubating an antibody with a test sample vary. Incubating conditions depend on the format employed in the assay, the detection methods employed the nature of the test sample, and the type and nature of the antibody used in the assay. One skilled in the art will recognize that any one of the commonly available immunological assay formats (such as, radioimmunoassays, enzyme-linked immunosorbent assays, diffusion based Ouchterlony, or rocket immunofluorescent assays, or the like) can readily be adapted to employ the antibodies of the present invention. Examples of such assays can be found in Chard, *"An Introduction to Radioimmunoassay and Related Techniques"* Elsevier Science Publishers, Amsterdam, The Netherlands (1986); Bullock et al., *"Techniques in Immunocytochemistry,"* Academic Press, Orlando, Fla. Vol. 1 (1982), Vol. 2 (1983), Vol. 3 (1985); Tijssen, *"Practice and Theory of Enzyme Immunoassays: Laboratory Techniques in Biochemistry and Molecular Biology,"* Elsevier Science Publishers, Amsterdam, The Netherlands (1985).

The anti-nNOS-II antibody and nNOS-inhibitors are also effective when immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling antibodies to such solid supports are well known in the art (Weir et al., *"Handbook of Experimental Immunology"* 4th Ed., Blackwell Scientific Publications, Oxford, England, Chapter 10 (1986), Jacoby et al., *Meth. Enzym.* 34 Academic Press, N.Y. (1974)).

Additionally, one or more of the antibodies used in the above described methods can be detectably labelled prior to use. Antibodies can be detectably labelled through the use of radioisotopes, affinity labels (such as, biotin, avidin, etc.), enzymatic labels (such as, horse radish peroxidase, alkaline phosphatase, etc.) fluorescent labels (such as, FITC or rhodamine, etc.), paramagnetic atoms, etc. Procedures for accomplishing such labelling are well-known in the art, for example, see Sternberger et al., *J. Histochem. Cytochem.* 18:315 (1970), Bayer et al., *Meth. Enzym.* 62:308 (1979), Engval et al., *Immunol.* 109:129 (1972), Goding, *J. Immunol. Meth.* 13:215 (1976). The labeled antibodies of the present invention can be used for in vitro, in vivo, and in situ assays to identify cells or tissues which express a specific protein or enzyme.

In an embodiment of the above methods, the antibodies are labeled, such that a signal is produced when the antibody (s) bind to the same molecule. One such system is described in U.S. Pat. No. 4,663,278.

The antibodies or antisense peptides of the present invention may be administered to a mammal intravenously, intramuscularly, subcutaneously, enterally, topically or parenterally. When administering antibodies or peptides by injection, the administration may be by continuous injections, or by single or multiple injections.

The antibodies or antisense peptides of the present invention are intended to be provided to a recipient mammal in a "pharmaceutically acceptable form" in an amount sufficient to be "therapeutically effective" or an "effective amount". As above, an amount is said to be therapeutically effective (an effective amount), if the dosage, route of administration, etc. of the agent are sufficient to affect the response to nNOS-II. Thus, the present antibodies may either stimulate or enhance the activity of the nNOS-II protein, resulting in increased NO synthesis, or they may inhibit or prevent the nNOS-II conversion of the peptide, oligopeptide or protein substrate into NO. Or, secondary antibody(s) may be designed to affect the response to the nNOS-II per se, i.e., an anti-antibody to nNOS-II. In the alternative, either an antibody or an anti-antibody may be designed to affect only the antisense strand of the molecule.

One skilled in the art can readily adapt currently available procedures to generate secondary antibody peptides capable of binding to a specific peptide sequence in order to generate rationally designed antipeptide peptides, for example see Hurby et al., "Application of Synthetic Peptides: Antisense Peptides", In *Synthetic Peptides, A User's Guide,* Freeman, N.Y., pp. 289–307 (1992), and Kaspczak et al., *Biochemistry* 28:9230–8 (1989). As used herein, an agent is said to be "rationally selected or designed" when the agent is chosen based on the configuration of the nNOS-II peptide.

To detect secondary antibodies, or in the alternative, the labelled primary antibody, labelling reagents may include, e.g., chromophobic, enzymatic, or antibody binding reagents which are capable of reacting with the labelled antibody. One skilled in the art will readily recognize that the disclosed antibodies of the present invention can readily be incorporated into one of the established kit formats which are well known in the art.

An antibody is said to be in "pharmaceutically or pharmacologically acceptable form" if its administration can be tolerated by a recipient patient. The antibodies of the present invention can be formulated according to known methods of preparing pharmaceutically useful compositions, whereby these materials, or their functional derivatives, are combined with a pharmaceutically acceptable carrier vehicle. Suitable vehicles and their formulation, inclusive of other human proteins, e.g., human serum albumin, are described, for example, in Remington's *Pharmaceutical Sciences,* 1980).

In order to form a pharmaceutically acceptable composition which is suitable for effective administration, such compositions will contain an effective amount of an antibody of the present invention together with a suitable amount of carrier. Such carriers include, but are not limited to saline, buffered saline, dextrose, water, glycerol, ethanol, and a combination thereof. The carrier composition may be sterile. The formulation should suit the mode of administration. In addition to carriers, the antibodies of the present invention may be supplied in humanized form.

Humanized antibodies may be produced, for example by replacing an immunogenic portion of an antibody with a corresponding, but non-immunogenic portion (i.e., chimeric antibodies) (Robinson et al., International Patent Publication PCT/US86/02269; Akira et al., European Patent Application 184,187; Taniguchi, European Patent Application 171,496; Morrison et al., European Patent Application 173,494; Neuberger et al., PCT Application WO 86/01533; Cabilly et al., European Patent Application 125,023; Better et al., *Science* 240:1041–1043 (1988); Liu et al., *Proc. Natl. Acad. Sci. USA* 84:3439–3443 (1987); Liu et al., *J. Immunol.* 139:3521–3526 (1987); Sun et al., *Proc. Natl. Acad. Sci. USA* 84:214–218 (1987); Nishimura et al., *Canc. Res.* 47:999–1005 (1987); Wood et al., *Nature* 314:446–449 (1985)); Shaw et al., *J. Natl. Cancer Inst.* 80:1553–1559 (1988)).

The compositions of the present invention can also include minor amounts of wetting or emulsifying agents, or pH buffering agents. The composition can be a liquid solution, suspension, emulsion, tablet, pill, capsule, sustained release formulation or powder. The composition can be formulated as a suppository with traditional binders and carriers such as triglycerides. Oral formulations can include standard carriers such as pharmaceutically acceptable mannitol, lactose, starch, magnesium stearate, sodium saccharine, cellulose, magnesium carbonate, etc.

In a preferred embodiment of the present invention, the compositions are formulated in accordance with routine procedures for intravenous administration to a subject. Typically, such compositions are carried in a sterile isotonic aqueous buffer. As needed, a composition may include a solubilizing agent and a local anesthetic. Generally, the components are supplied separately or as a mixture in unit dosage form, such as a dry lyophilized powder in a sealed container with an indication of active agent. Where the composition is administered by infusion, it may be provided with an infusion container with a sterile pharmaceutically acceptable carrier. When the composition is administered by injection, an ampoule of sterile water or buffer may be included to be mixed prior to injection.

The therapeutic compositions may also be formulated in salt form. Pharmaceutically acceptable salts include those formed with free amino groups, such as those derived from hydrochloric, phosphoric, acetic, oxalic and tartaric acids, or formed with free carboxyl groups such as those derived from sodium, potassium, ammonium, calcium, ferric hydroxides. isopropylamine, triethylamine, 2-ethylamino ethanol, histidine, procaine, etc.

The dosage of the administered agent will vary depending upon such factors as the patient's age, weight, height, sex, general medical condition, previous medical history, etc. In general, it is desirable to provide the recipient with a dosage of the antibody which is in the range of from about 1 pg/kg to 10 mg/kg (body weight of patient), although a lower or higher dosage may be administered. Suitable ranges for intravenous administration is typically about 20–500 μg of active compound per kilogram body weight. Effective doses may be extrapolated from dose-response curves derived from in vitro and in vivo animal model test systems.

Since highly purified proteins are now available, X-ray crystallography and NMR-imaging techniques can be used to identify the structure of the enzyme. Utilizing such information, computer modeling systems are now available that allows one to "rationally design" an agent capable of binding to a defined structure (Hodgson, *Biotechnology* 8:1245–1247 (1990)) (Hodgson, *Biotechnology* 9:609–613 (1991)). As used herein, an agent is said to be "rationally designed" if it is selected based on a computer model of nNOS-II.

In another embodiment of the present invention, methods are provided for modulating the translation of RNA encoding nNOS-II protein in the cell. Specifically, said method comprises introducing into a cell a DNA sequence which is capable of transcribing RNA which is complimentary to the RNA encoding the nNOS-II protein. By introducing such a DNA sequence into a cell, antisense RNA will be produced which will hybridize and block the translation of the nNOS-II protein. Antisense cloning has been described by Rosenberg et al., *Nature* 313:703–706 (1985), Preiss et al., *Nature* 313:27–32 (1985), Melton, *Proc. Natl. Acad. Sci. USA* 82:144–148 (1985) and Kim et al., *Cell* 42:129–138 (1985).

Transcription of the introduced DNA will result in multiple copies of antisense RNA which will be complimentary to the nNOS-II. By controlling the level of transcription of antisense RNA, and the tissue specificity of expression, one skilled in the art can regulate the level of activity of nNOS-II in specific cells within a patient.

In another embodiment of the present invention, kits are provided which contain the necessary reagents to carry out the previously described methods and assays.

All essential publications mentioned herein are hereby incorporated by reference.

In order that those skilled in the art can more fully understand this invention, the following examples are set forth. These examples are included solely for the purpose of illustration, and should not be considered as expressing limitations unless so set forth in the appended claims.

Examples

In the following examples and protocols, restriction enzymes, ligase, labels, and all commercially available reagents were utilized in accordance with the manufacturer's recommendations. The cell and molecular and protein purification methods utilized in this application are established in the art and will not be described in detail. However, standard methods and techniques for isolation, purification, labeling, and the like, as well as the preparation of standard reagents may be performed essentially in accordance with *Molecular Cloning: A Laboratory Manual, 2nd ed.,* edited by Sambrook, Fritsch & Maniatis, Cold Spring Harbor Laboratory, 1989, and the revised third edition thereof, or as set forth in the literature references cited and incorporated herein. Methodologic details may be readily derived from the cited publications.

Example 1

Isolation, Purification and Characterization of nNOS-II

Using the following materials and methods, substantially pure nNOS-II protein was prepared and purified from crude supernatant preparations from rat cerebellum, and characterized as containing calmodulin-independent NOS activity capable of catalyzing the oxidation of an arginine-rich nonapeptide, BK, to produce NO.

Materials: BK, [Thi$^{5,8}$,D-Phe$^7$]-BK, and [N-adamantaneacetyl-D-Arg$^0$, Hyp$^3$, Thi$^5$,8, D-Phe$^7$]-BK were purchased from American Peptide Co. (San Diego, Calif.). Cit$^1$-BK was synthesized (University of Iowa, Protein Structure Facility) by solid phase synthesis using 2-chlorotrityl chloride resin (Barlos et al., *Int. J. Peptide Protein Res.* 37:513–520 (1991)). The synthetic peptide Cit$^1$-BK was greater than 98% pure by HPLC, and gave m/z 1061.3 by laser desorption mass spectrometry. (6R)-5,6,7,8-Tetrahydrobiopterin (BH$_4$) was from Biochemical Research Inc. (Natick, Mass.). L-arginine, N$^G$-methyl-L-arginine (L-NMA), N$^G$-nitro-L-arginine (L-NNA), 2',5'-ADP-agarose and other reagents were purchased from Sigma Chemical Co. (St Louis, Mo.).

Enzyme Purification: Ten cerebella taken from Sprague Dailey rats (male, 250–350 g) were homogenized in 50 mL of ice-cold buffer A {10 mM Tris-HCl (pH 7.5) containing 1 mM DTT, 1 mM EDTA}. All subsequent purification procedures were carried out at 4° C. The homogenate was centrifuged at 100,000×g for 120 min, and the supernatant was loaded onto a 25 mL DEAE-agarose column equilibrated with buffer A. The column was washed with 50 mL buffer A and eluted with a 200 mL linear gradient of 0–500 mM NaCl in buffer A. Fractions (4 mL) were collected and assayed for enzyme activity.

Figure 1:
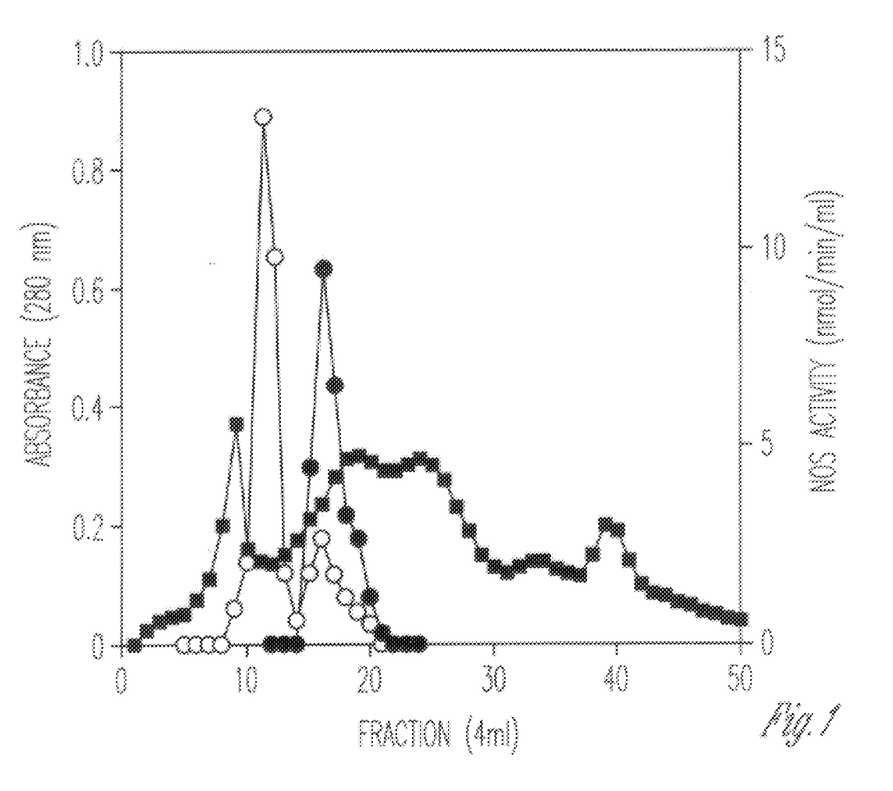
FIG. 1 depicts a DEAE-agarose column elution profile for both NOS enzymes from rat cerebellum. L-arginine (○) NOS activity (calmodulin dependent), and BK (●) NOS activity (calmodulin independent). Protein absorbance at 280 nm (□) from rat cerebellum was used to monitor the eluting process.

Elution profiles similar to those observed by Bredt et al. (*Proc. Natl Acad. Sci. USA* 87:682–685 (1990)) reproducibly gave two calmodulin-dependent NOS activity peaks with L-arginine as substrate (see FIG. 1, fractions 8–21 (◯)). However, only one of these (FIG. 1, fractions 15–21 (●)) displayed calmodulin-independent NOS activity with BK as substrate. Protein absorbance at 280 nm (FIG. 1, □) from rat cerebellum was used to monitor the eluting process.

Fractions representing the active peak for BK from the DEAE-agarose column were pooled and concentrated to 15 mL by membrane ultrafiltration, and loaded onto a 5 mL, 2',5'-ADP-agarose column equilibrated with buffer B {10 mM Tris-HCl (pH 7.0) containing 1 mM DTT, 1 mM EDNA, and 10% glycerol}. The column was subsequently washed with 20 mL of buffer B, 10 mL of 0.5M NaCl in buffer B, 10 mL of 0.5 mM NADH in buffer B, 10 mL of 0.5 mM NADP$^+$ in buffer B, and 20 mL of buffer B. The NOS activity was finally eluted with 10 mL of 10 mM NADPH in buffer B.

The affinity eluate was concentrated to 1.5 mL and loaded onto a 5 mL DEAE-agarose column equilibrated with buffer B. The column was washed with 20 mL buffer B and eluted with a 100 mL linear gradient of 0–300 mM NaCl in buffer B. Fractions (2 mL) were collected and assayed for enzyme activity, and active fractions (8 mL) were pooled and concentrated to 0.2–0.5 mL with an Amicon PM-30 membrane to afford a 6,360-fold purified enzyme preparation. The thus-purified, novel constitutive neuronal NOS was designated as nNOS-II to differentiate it from the NOS isoform (nNOS) previously described by Bredt et al., supra (1990).

The purification of nNOS-II is summarized in Table 2:

TABLE 2

Purification of nNOS-II from rat cerebellum.*

| Step | Total Protein (μg) | Total Activity (nmol/min) | Specific Activity (nmol/min/mg protein) | Recovery (%) | Purification Factor (fold) |
| --- | --- | --- | --- | --- | --- |
| Cytosol | 356,640 | 44.18 | 0.19 | 100 | 1 |
| DEAE-agarose | 69,200 | 27.20 | 0.39 | 61.6 | 2 |
| ADP-agarose | 66 | 19.10 | 289.1 | 43.2 | 1,522 |
| DEAE-agarose | 4 | 4.64 | 1,208.3 | 10.5 | 6,360 |

*Values of final specific activities, recovery and fold-purification represent the means of three enzyme preparations. Enzyme activity was measured spectophotometically. BK (100 μM) was used for enzyme assay during enzyme purification, and enzymatic reactions were initiated by the addition of protein. Protein was determined using the Bradford protein assay.

NOS Activity Assay: NOS activity was determined spectrophotometrically by the rapid and quantitative oxidation of oxyhemoglobin to methemoglobin (Feelish et al., *Eur. J. Pharmacol.* 139:19–30 (1987); Olken et al., *Biochem. Biophys. Res. Commun.* 177:828–833 (1991)).

Like previously characterized nNOS from cerebellum, nNOS-II requires NADPH, FAD, FMN, $Ca^{2+}$, and $BH_4$ with BK as substrate. Thus, reaction mixtures for NOS assays containing 50 mM Tris-HCl buffer (pH 7.5), were optimized to contain 4 μM oxyhemoglobin, 100 μM NADPH, 1 mM $CaCl_2$, 10 μM FAD, 10 μM FMN, 20 μM $BH_4$, 150 μM DTT, 100 μM BK or L-arginine and 0.1–3 μg enzyme in a final volume of 0.5 mL.

nNOS-II has stabilities similar to nNOS. In addition, nNOS-II also oxidizes L-arginine, but only when calmodulin is added along with the other cofactors. Thus, calmodulin (10 μg/mL) was added to the reaction mixtures when L-arginine was used as substrate.

Determinations of Molecular Weight: The molecular mass of the denatured purified enzyme was determined by sodium dodecyl sulfate-polyacrylamide gel electrophoresis (SDS-PAGE) to be approximately 105 kD (see, FIG. 2). The apparent native molecular mass of the enzyme was approximately 230 kD by gel filtration, indicating that nNOS-II is a homodimeric protein.

Figure 2:
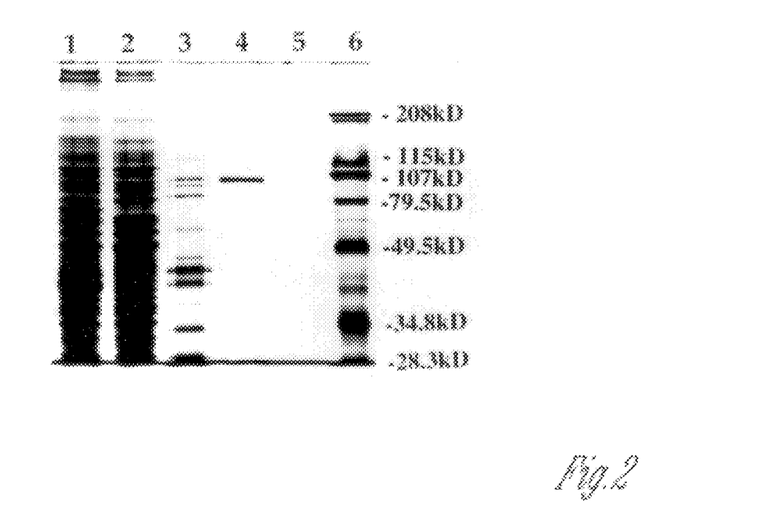
FIG. 2 depicts an 8%, silver-stained SDS-polyacrylamide gel showing: Lane 1, cytosol (10 μg protein); Lane 2, eluate from first DEAE-column (10 μg); Lane 3, NADPH eluate from 2',5'-ADP-agarose column (2 μg protein); Lane 4, eluate from second DEAE-agarose column containing purified enzyme (0.5 μg protein); Lane 5, control with sample buffer; Lane 6, molecular weight markers (Bio-Rad) of myosin (208,000), b-galactosidase (115,000) phosphorylase B (107,000), bovine serum albumin (79,500), ovalbumin (49,500), carbonic anhydrase (34,800), soybean trypsin (28, 300).

The native molecular weight of the purified enzyme was estimated by analytical gel filtration chromatography carried out using an Alltech Macrosphere 150 column (7 μm, 4.6×25 cm) and a mobile phase of 10 mM Tris-HCl buffer (pH 7.5) containing 1 mM DTT and 0.2M NaCl, which was used to equilibrate the column and to elute protein samples at a flow rate of 0.5 mL/min. Eluting protein peaks (retention volumes, $R_V$) were monitored at 280 nm. Standard proteins ($M_r$) used (as shown in FIG. 2) were bovine thyroglobulin (669,000, $R_V$ 1.83 mL), horse spleen apoferritin (443,000, $R_V$ 1.97 mL), sweet potato β-amylase (200,000, $R_V$ 2.28 nL), yeast alcohol dehydrogenase (150,000, $R_V$ 2.47 mL), and bovine serum albumin (66,000, $R_V$ 2.78 mL).

The peak ($R_V$ 2.25 mL) corresponding to the eluted enzyme (230,000) was collected and assayed for NOS activity.

Kinetic Determinations: Since BK contains both N- and C-terminal arginines, it was possible that BK could give rise to NO plus three different nonapeptide products including: $Cit^1$-BK, $Cit^9$-BK and $Cit^1,Cit^9$-BK. HPLC and amino acid sequencing were used to isolate and identify the nonapeptide product formed when nNOS-II oxidized BK. Kinetic experiments were conducted using the standard enzyme assay described above.

a) Isolation of Enzymatic Products by High Performance Liquid Chromatography (HPLC): Enzymatic reaction mixtures contained 0.5 μg purified enzyme, 50 mM Tris-HCl buffer (pH 7.5), 100 μM NADPH, 20 μM FAD, 20 μM FMN, 1 mM $CaCl_2$, 50 μM tetrahydrobiopterin, and 100 μM substrate in final volumes of 0.5 mL. Reaction mixtures were incubated for 120 min at 37° C., and transferred to microconcentrators (Mr cut-off 10,000, Bio-Rad) and centrifuged to remove the enzyme. Fractions through the concentrator membrane were subjected to HPLC analyses. HPLC was performed with a Shimadzu LC-10AD pump and a SPD-M6A photodiode array UV-Vis detector set at 214–219 nm. Samples of 15 μL were resolved on a μBondapak C18 column (Waters; 10 mm; 3.9×300 mm, inside diameter) preceded by a guard column (3.9×20 mm) at a flow rate of 1 mL/min. The mobile phase consisted of mixtures of: A. 0.1% trifluoroacetic acid in water; B. 0.095% trifluoroacetic acid in acetonitrile.

Elution was achieved with the following gradients: 0–15 min, 0–15% linear gradient of B; 15–35 min, 15–20% linear gradient of B; and 35–40 min, 20-0% linear gradient of B. Retention times for BK, $Cit^1$-BK, and $Cit^1,Cit^9$-BK are 22.8 min, 24.3 min, and 26.3 min, respectively.

For amino acid sequencing, reaction mixture samples of 200 μL were injected, and peaks at 26.3 min were collected and concentrated. Incubations without substrate and without purified enzyme were used and analyzed as controls.

b) Amino Acid Sequencing: Amino acid sequencing was determined by automated microsequencing with Edman degradation reactions on a 475A Sequencer (Applied Biosystems, Inc.) in the University of Iowa, Protein Structure Facility. The enzymatic product (2 μg) from HPLC (see, FIGS. 3A and B) was sequenced in duplicate to confirm the peptide sequence.

c) Kinetic Data: To determine $K_M$ values for BK, $Cit^1$-BK and L-arginine, the substrate concentrations used were 3.125, 6.25, 12.5, 25, and 50 μM. L-NMA and L-NNA, at concentrations of 0, 3.125, 6.25, 12.5, 25, and 50 μM, were used to measure Ki values in the presence of above concentrations of BK. N-adamantaneacetyl-[D-$Arg^0$, $Hyp^3$, $Thi^{5,8}$, D-$Phe^7$]-BK, at concentrations of 0, 0.625, 1.25, 2.5, 5, and 10 μM, was used to determine its Ki value in the presence of the concentrations of BK given above. Kinetic data were calculated by fitting experimental data to the EZ-FIT program (Perrella, *Anal. Biochem.* 174:437–447 (1988)).

Figure 3A:
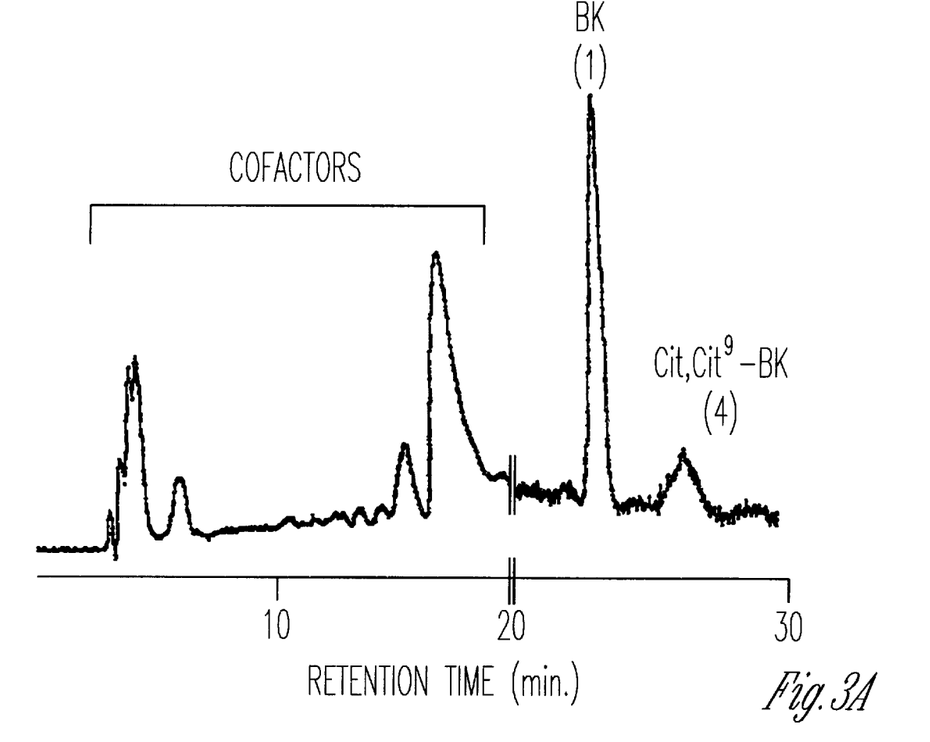
FIG. 3A is a chromatogram of the enzymatic reaction in which BK is the substrate.
Figure 3B:
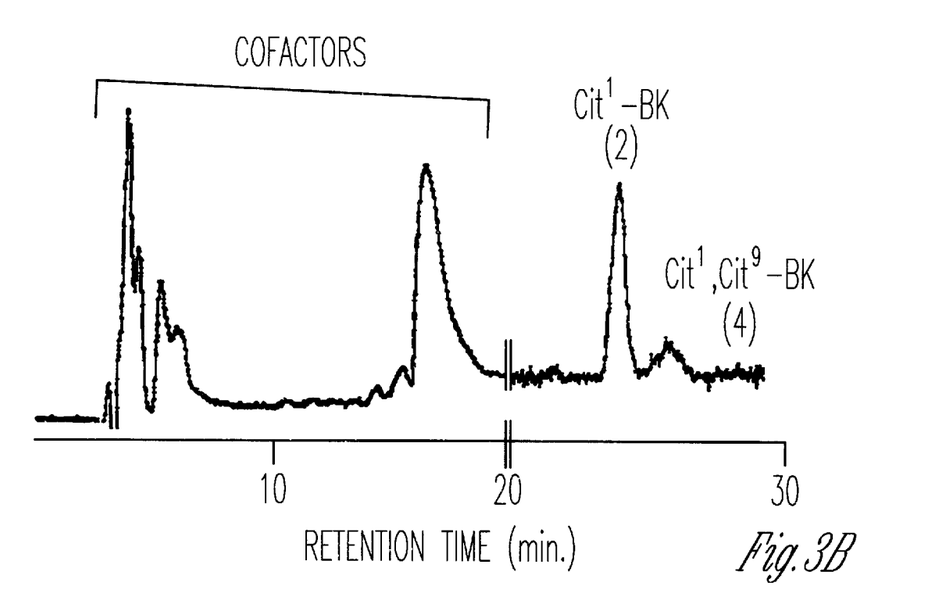
FIG. 3B is a chromatogram of the enzymatic reaction in which $Cit^1$-BK is the substrate.

The only peptide product obtained during the nNOS-II oxidation of BK was $Cit^1,Cit^9$-BK, where both N- and C-terminal BK-arginines were converted to their corresponding citrullines (FIG. 3A). The synthetic nonapeptide $Cit^1$-BK in which N-terminal arginine was replaced with citrulline was also a substrate for nNOS-II, and it, too, gave Cit$^1$,Cit$^9$-BK (FIG. 3B). Difficulties encountered in synthesizing Cit$^9$-BK precluded its use in the present investigations.

Apparent K$_M$ values for BK and Cit$^1$-BK were 8.5 and 6.2 μM respectively, while apparent V$_{max}$ values for BK and Cit$^1$-BK were 1.2 and 1.6 μmol/min/mg protein, respectively. The kinetic results suggest that neither Cit$^1$-BK nor Cit$^9$-BK are likely to accumulate as products during the course of nNOS-II oxidations of BK.

By comparison, the apparent K$_M$ of nNOS-II for L-arginine was 10.6 μM, slightly higher than the reported value of 2 μM for previously described nNOS (Bredt et al., *Proc. Natl Acad. Sci. USA* 87:682–685 (1990)). With L-arginine as substrate, nNOS-II and nNOS display apparent V$_{max}$ values of 0.85 and 0.96 μmol/min/mg protein, respectively.

With nNOS-II and BK as substrate, typical NOS inhibitors, L-NMA and L-NNA, are reversible, competitive inhibitors with apparent Ki values of 8.6 μM and 23.8 μM, respectively. These Ki values are, however, significantly different from previously established Ki values for L-NMA of 1.4 μM and L-NNA of 4.4 μM with L-arginine as substrate for nNOS (Nathan, *FASEB J.* 6:3051–3064 (1992); Marletta, *J. Biol. Chem.* 268:12231–12234 (1993); Knowles et al., *Biochem. J.* 298:249–258 (1994); Griffith et al., *Annu. Rev. Physiol.* 57:707–736 (1995)).

In addition, known potent specific B2 receptor antagonists [N-adamantaneacetyl-D-Arg$^0$, Hyp$^3$, Thi$^{5,8}$, D-Phe$^7$]-BK and [Thi$^{5,8}$, D-Phe$^7$]-BK (Lammek et al., *Peptides* 11:1041–1043 (1990); Lammek et al., *J. Phar. Pharmacol.* 43:887–888 (1988); Austin et al., *J. Physiol.* 478:351–356 (1994)) were examined for their possible effects with regard to nNOS-II activity. While [N-adamantaneacetyl-D-Arg$^0$, Hyp$^3$, Thi$^{5,8}$, D-Phe$^7$]-BK competitively inhibited nNOS-II activity on BK, with an apparent Ki of 2.5 mM, [Thi$^{5,8}$, D-Phe$^7$]-BK had no effect on nNOS-II activity over a concentration range of 0.5–100 mM.

In view of these findings, it is believed that natural endogenous peptide substrates other than BK exist for nNOS-II. It is also believed that oligopeptide-utilizing endothelial and macrophage NOSs will be found. The broad implications of this discovery are that arginine-rich peptides of greater or lesser size than BK can serve as NOS substrates to form NO, and that natural or synthetic peptides, oligopeptides or proteins can function as NOS.

Although the present invention has been described with reference to the presently preferred embodiments, the skilled artisan will appreciate that various modifications, substitutions, omissions and changes may be made without departing from the spirit of the invention. Accordingly, it is intended that the scope of the present invention be limited only by the scope of the following claims, including equivalents thereof.

What is claimed is:

1. A nitric oxide synthase (NOS) protein (nNOS-II), purified from rat brain, said protein having a denatured molecular mass as determined by sodium dodecyl sulfate polyacrylamide gel electrophoresis under reducing conditions of about 105 kD, and a native homodimeric molecular mass as determined by gel filtration of about 230 kD, requiring FAD, FMN, $Ca^{2+}$ and tetrahydrobiopterin cofactors for the production of nitric oxide either from L-arginine, or an analog or derivative thereof, or from an arginine-rich peptide, oligopeptide, or protein substrate, and further providing that the NOS protein is calmodulin-dependent with L-arginine as a substrate and calmodulin-independent with an arginine-rich polypeptide as a substrate, wherein the NOS protein is purified to specific activity at least 6,360-fold that of a crude tissue preparation.

2. The NOS protein of claim 1, wherein the activity of the protein is calmodulin-dependent when L-arginine is a substrate.

3. The NOS protein of claim 2, further having a $K_M$ value of approximately 10.6 $\mu$M for L-arginine as a substrate and sufficient calmodulin is present to act as a cofactor.

4. The NOS protein of claim 2, further having a $V_{max}$ value of 0.85 $\mu$mol/min/mg protein.

5. The NOS protein of claim 1, wherein the activity of the protein is calmodulin-independent when an arginine-rich polypeptide, peptide or oligopeptide is a substrate.

6. The NOS protein of claim 5, wherein the arginine-rich polypeptide substrate is bradykinin.

7. The NOS protein of claim 6, wherein NOS activity is competitively inhibited by $N^G$-methyl-, $N^G$-nitro-L-arginines and by BK receptor-antagonists, including oligopeptide BK receptor-antagonists.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( C ) STRANDEDNESS: Not Relevant
        ( D ) TOPOLOGY: unknown     ( i i ) MOLECULE TYPE: peptide     ( v ) FRAGMENT TYPE: N-terminal     ( v i i ) IMMEDIATE SOURCE:
        ( B ) CLONE: bradykinin (BK)

( x i ) SEQUENCE DESCRIPTION: SEQ ID NO:1:

Arg  Pro  Pro  Gly  Phe  Ser  Pro  Phe  Arg
    1                           5

( 2 ) INFORMATION FOR SEQ ID NO:2:

( i ) SEQUENCE CHARACTERISTICS:
        ( A ) LENGTH: 8 amino acids
        ( B ) TYPE: amino acid
        ( C ) STRANDEDNESS: Not Relevant
        ( D ) TOPOLOGY: unknown     ( i i ) MOLECULE TYPE: peptide     ( v ) FRAGMENT TYPE: C-terminal     ( v i i ) IMMEDIATE SOURCE:
        ( B ) CLONE: Des-Arg1-BK     ( x i ) SEQUENCE DESCRIPTION: SEQ ID NO:2:

```
       Pro  Pro  Gly  Phe  Ser  Pro  Phe  Arg
        1              5
```

( 2 ) INFORMATION FOR SEQ ID NO:3:

( i ) SEQUENCE CHARACTERISTICS:
        ( A ) LENGTH: 8 amino acids
        ( B ) TYPE: amino acid
        ( C ) STRANDEDNESS: Not Relevant
        ( D ) TOPOLOGY: unknown     ( i i ) MOLECULE TYPE: peptide     ( v ) FRAGMENT TYPE: N-terminal     ( v i i ) IMMEDIATE SOURCE:
        ( B ) CLONE: Des-Arg9-BK     ( x i ) SEQUENCE DESCRIPTION: SEQ ID NO:3:

```
       Arg  Pro  Pro  Gly  Phe  Ser  Pro  Phe
        1              5
```

( 2 ) INFORMATION FOR SEQ ID NO:4:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: unknown     ( i i ) MOLECULE TYPE: peptide     ( v ) FRAGMENT TYPE: N-terminal     ( v i i ) IMMEDIATE SOURCE:
        ( B ) CLONE: bradykinin (BK) fragment 1-7

( x i ) SEQUENCE DESCRIPTION: SEQ ID NO:4:

```
       Arg  Pro  Pro  Gly  Phe  Ser  Pro
        1              5
```

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: unknown     ( i i ) MOLECULE TYPE: peptide     ( v ) FRAGMENT TYPE: N-terminal     ( v i i ) IMMEDIATE SOURCE:
        ( B ) CLONE: bradykinin (BK) fragment 1-5

( x i ) SEQUENCE DESCRIPTION: SEQ ID NO:5:

```
       Arg  Pro  Pro  Gly  Phe
        1              5
```

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( C ) STRANDEDNESS: Not Relevant
        ( D ) TOPOLOGY: unknown     ( i i ) MOLECULE TYPE: peptide     ( v ) FRAGMENT TYPE: internal     ( v i i ) IMMEDIATE SOURCE:

( B ) CLONE: bradykinin (BK) fragment 2-7

( x i ) SEQUENCE DESCRIPTION: SEQ ID NO:6:

Pro Pro Gly Phe Ser Pro
1               5

( 2 ) INFORMATION FOR SEQ ID NO:7:

( i ) SEQUENCE CHARACTERISTICS:
      ( A ) LENGTH: 9 amino acids
      ( B ) TYPE: amino acid
      ( C ) STRANDEDNESS: Not Relevant
      ( D ) TOPOLOGY: unknown    ( i i ) MOLECULE TYPE: peptide    ( v ) FRAGMENT TYPE: C-terminal    ( v i i ) IMMEDIATE SOURCE:
      ( B ) CLONE: [Lys1]-BK    ( x i ) SEQUENCE DESCRIPTION: SEQ ID NO:7:

Lys Pro Pro Gly Phe Ser Pro Phe Arg
1               5

( 2 ) INFORMATION FOR SEQ ID NO:8:

( i ) SEQUENCE CHARACTERISTICS:
      ( A ) LENGTH: 10 amino acids
      ( B ) TYPE: amino acid
      ( C ) STRANDEDNESS: Not Relevant
      ( D ) TOPOLOGY: unknown    ( i i ) MOLECULE TYPE: peptide    ( v ) FRAGMENT TYPE: N-terminal    ( v i i ) IMMEDIATE SOURCE:
      ( B ) CLONE: Lys-BK    ( x i ) SEQUENCE DESCRIPTION: SEQ ID NO:8:

Lys Arg Pro Pro Gly Phe Ser Pro Phe Arg
1               5               10

( 2 ) INFORMATION FOR SEQ ID NO:9:

( i ) SEQUENCE CHARACTERISTICS:
      ( A ) LENGTH: 11 amino acids
      ( B ) TYPE: amino acid
      ( C ) STRANDEDNESS: Not Relevant
      ( D ) TOPOLOGY: unknown    ( i i ) MOLECULE TYPE: peptide    ( v ) FRAGMENT TYPE: N-terminal    ( v i i ) IMMEDIATE SOURCE:
      ( B ) CLONE: Ile-Ser-BK    ( x i ) SEQUENCE DESCRIPTION: SEQ ID NO:9:

Ile Ser Arg Pro Pro Gly Phe Ser Pro Phe Arg
1               5               10

( 2 ) INFORMATION FOR SEQ ID NO:10:

( i ) SEQUENCE CHARACTERISTICS:
      ( A ) LENGTH: 11 amino acids
      ( B ) TYPE: amino acid
      ( C ) STRANDEDNESS: Not Relevant
      ( D ) TOPOLOGY: unknown    ( i i ) MOLECULE TYPE: peptide ( v ) FRAGMENT TYPE: N-terminal ( v i i ) IMMEDIATE SOURCE:
    ( B ) CLONE: Met-Lys-BK ( x i ) SEQUENCE DESCRIPTION: SEQ ID NO:10:

```
Met Lys Arg Pro Pro Gly Phe Ser Pro Phe Arg
 1               5                   10
```